US012788803B2

(12) United States Patent
Schjoldager

(10) Patent No.: US 12,788,803 B2
(45) Date of Patent: Nov. 10, 2026

(54) HAEMORRHAGE INHIBITING COMPOSITIONS AND METHODS INVOLVING THE SAME

(71) Applicant: Stellaris Pharmaceuticals ApS, Copenhagen V (DK)

(72) Inventor: Birgit Ter-Borch Gram Lilienfeldt Schjoldager, Copenhagen V (DK)

(73) Assignee: STELLARIS PHARMACEUTICALS APS, Copenhagen V (DK)

( * ) Notice: Subject to any disclaimer, the term of this patent is extended or adjusted under 35 U.S.C. 154(b) by 13 days.

(21) Appl. No.: 18/210,190

(22) Filed: Jun. 15, 2023

(65) Prior Publication Data

US 2024/0066106 A1 Feb. 29, 2024

(51) Int. Cl.

| | |
|---|---|
| ***A61K 38/48*** | (2006.01) |
| ***A61K 9/00*** | (2006.01) |
| ***A61K 38/00*** | (2006.01) |
| ***A61P 7/04*** | (2006.01) |

(52) U.S. Cl.

CPC ........ *A61K 38/4846* (2013.01); *A61K 9/0036* (2013.01); *A61K 38/00* (2013.01); *A61P 7/04* (2018.01)

(58) Field of Classification Search

CPC .. A61K 38/4846; A61K 9/0036; A61K 38/00; A61P 7/04

See application file for complete search history.

(56) References Cited

U.S. PATENT DOCUMENTS 8,461,115 B2 * 6/2013 Uttenthal ........... A61K 38/4846 530/380

OTHER PUBLICATIONS

Karalapillai and Popham, International Journal of Obstetric Anesthesia (2007) 16, 29-34 (Year: 2007).*
Morlando & Collins, International Journal of Women's Health 2020:12 1033-1045 (Year: 2020).*
Bagga et al., MedGenMed 2004 6(1):50 (Year: 2004).*
Schjoldager et al., AJOG, Jun. 2017, 608.e1-e5 (Year: 2017).*
Maier, AJOG, Aug. 1993, 169, 317-323 (Year: 1993).*
Van Buren, Gleanings from Our Exchanges, pp. 161-163, stated to be from New York Medical Journal, Mar. 1875 (Year: 1875).*
Rao et al., ACS Appl. Mater. Interfaces 2021, 13, 10689-10704 (Year: 2021).*
Wang et al., Taiwanese Journal of Obstetrics & Gynecology 55 (2016) 301-302 (Year: 2016).*
Grotegut et al., Am J Obstet Gynecol. Jan. 2011; 2014(1), 12 pages (supplied May 21, 2024 by applicant) (Year: 2014).*
Tahla Burki, www.thelancet.com, vol. 402, 2023, p. 601 (Year: 2023).*
Balki et al., www.anethesia-analgesia.org, May 2016, vol. 122, No. 5, 1508-1515 (supplied May 21, 2024 by applicant) (Year: 2016).*
McDonald et al., J Midwifery Women's Health 2007;52:254-271, 2007 (Year: 2007).*
Zdanowicz et al., J. Clin. Med. 2023, 12, 7471, 11 pages (Year: 2023).*
Werner H. Rath, Nordic Federation of Societies of Obstetrics and Gynecology 90 (2011) 421â428 (Year: 2011).*
Grotegut et al., Am J Obstet Gynecol. Jan. 2011; 2014(1), 12 pages (Year: 2014).*
Gallos, et al., "Prognostic accuracy of clinical markers of postpartum bleeding in predicting maternal mortality or severe morbidity: a WHO individual participant data meta-analysis." The Lancet, 2025; 406(10514):p. 1969-p. 1982.
Consolidated guidelines for the prevention, diagnosis and treatment of postpartum haemorrhage. Geneva: World Health Organization; 2025.
Danish Society of Obstetrics and Gynaecology (DSOG) guidelines for treatment of PPH, 2017 (English translation provided).

* cited by examiner

*Primary Examiner* — Joseph Fischer
(74) *Attorney, Agent, or Firm* — Weston R. Gould; DINSMORE & SHOHL LLP

(57) ABSTRACT

The present disclosure relates to compositions, solutions, and patches as well as methods for using the same in treatment, prevention, or amelioration of haemorrhage in a subject. In particular, the present disclosure relates to methods for topical treatment, prevention, or amelioration of postpartum haemorrhage in a subject.

12 Claims, 2 Drawing Sheets

HAEMORRHAGE INHIBITING COMPOSITIONS AND METHODS INVOLVING THE SAME

CROSS REFERENCE TO RELATED APPLICATIONS

Figure 1:
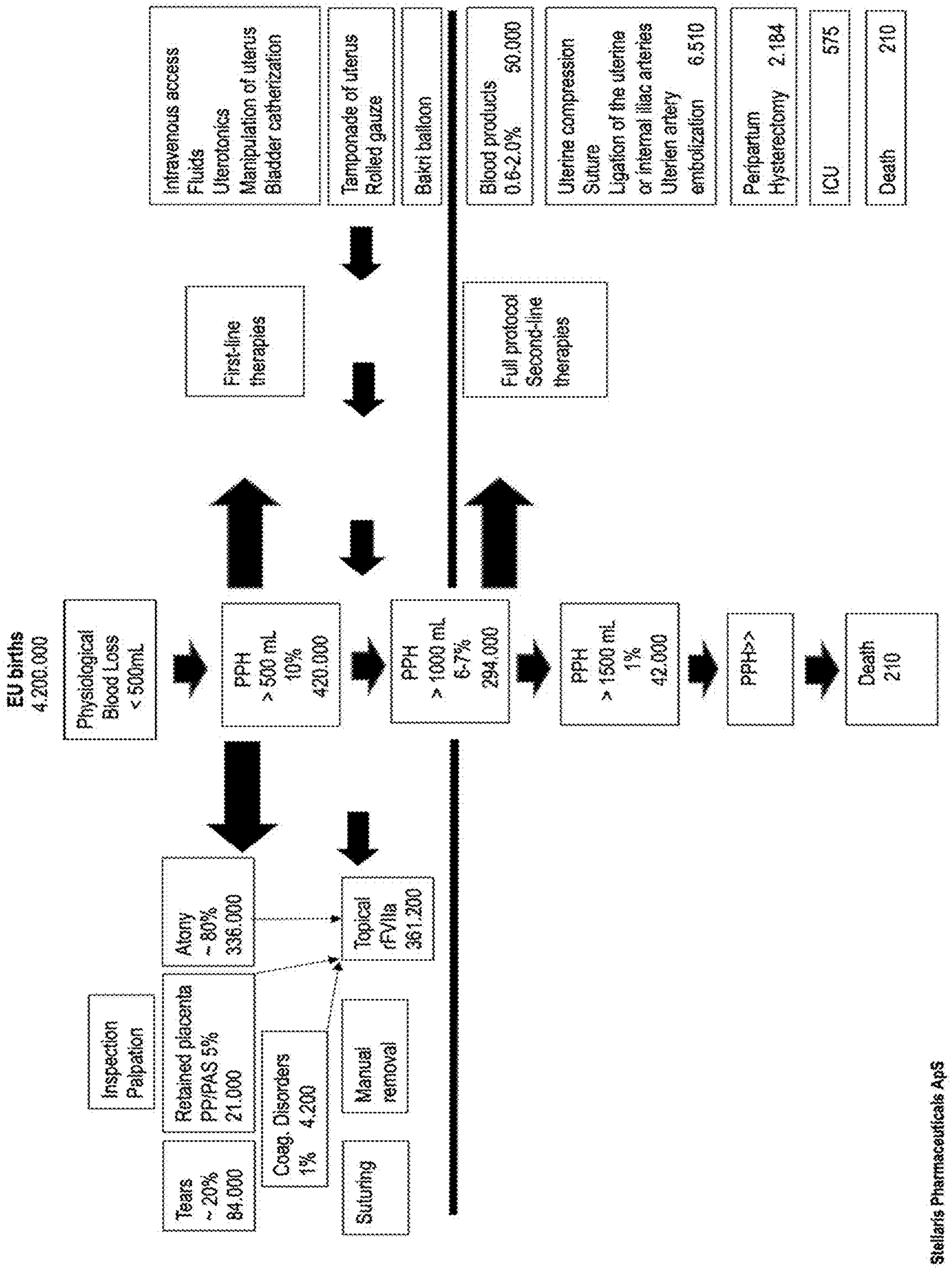

This application depends from and claims priority to European Patent Application No: EP22192409.5 filed Aug. 26, 2022, the entire contents of which are incorporated herein by reference.

TECHNICAL FIELD

The present invention relates to compositions, solutions, and medical dressings as well as methods for using the same in treatment, prevention or amelioration of hemorrhage in a subject. In particular, the present invention relates to methods for topical treatment, prevention, or amelioration of uterotonic resistant postpartum hemorrhage in a subject.

BACKGROUND

Blood loss (hemorrhage) is a serious and potentially life-threatening medical condition. In particular among puerperal women health-threatening hemorrhage represents a significant risk. Postpartum Hemorrhage (PPH) may be defined as: >500 mL blood loss (~10% of deliveries (5-15%), severe PPH>1000 mL (~6-7%), PPH>1500 mL (~1-2%), massive life-threatening >2500 mL or hypovolemic shock, within 24 hours after delivery of the child (~0.24%). PPH comprises the greatest risk of dying for any fertile woman. PPH materializes during the third phase of delivery i.e., the time between delivery of the child and the delivery of the placenta and may continue beyond. It is crucial to know that PPH comes abruptly and rarely is predictable. Despite known risk factors such as multipara, previous PPH, pregnancy-induced hypertension, macrosomia, chorioamnionitis, episiotomy, instrumental CD or VD—⅔ of women who suffer PPH had no prior risk for PPH. Time and the magnitude of blood loss are factors both working against the rescuing of the mother.

Haemostasis consists of a primary phase of vasoconstriction and production of a short-lived plug of platelets and fibrin, the second phase occurs concomitantly and produces a stable clot through coagulation, the third stage concludes the trimming of the clot and involves anticoagulation measure by passing fibrinolytics.

Coagulation involves two pathways, a slow intrinsic and a fast extrinsic, they emerge into a common pathway. The intrinsic pathway is activated upon an intravascular trauma through exposed endothelial collagen inside the vascular system and involves the factors XII, XI, IX, VIII, prothrombin to thrombin, fibrinogen to soluble fibrin, and to solid fibrin by XIIIa. The time to form a clot is measured by the activated partial thromboplastin time (APTT): 25-50 seconds. The extrinsic pathway is set off upon external damage to a vessel and involves tissue factor (TF) and Factor VIIa/VII (FVIIa/FVII), converting X to Xa, prothrombin to thrombin, fibrinogen to soluble fibrin, and to solid fibrin by XIIIa. The TF/FVIIa complexing activates a coagulation cascade that mounts to $10^6$-fold of the basal coagulation. The time to form a clot after exposure to TF, is measured by the prothrombin time being 12-13 seconds. Factor VII circulates in a zymogen form FVII (99%) and in its activated form FVIIa (1%), and half-life in plasma is approximately 2.5 hours. Since its cofactor TF is bound to cell surfaces on cells exterior to the blood vessels, FVII is the only procoagulant that can circulate in its active form without triggering the coagulation cascade.

The principal causes of PPH: Atony (75-80%), trauma (20%), placenta previa (PP)/Placenta Accreta Spectrum (PAS) (5%), coagulative disorders (1%). Seldom PPH is due to abruptio placenta or Inversio Uteri.

Atony is a condition where the uterine muscle fails to contract after delivery. It is seen after Induced or augmented labor, preeclampsia, chorioamnionitis, obesity, multiple gestation, polyhydramnios, prolonged second stage of labor, the placenta may be retained.

PP is a condition where the placenta is implanted so that the internal orifice of the cervix is covered, PP happens in 0.05-0.4% of pregnancies or 4% of PPH. PAS is a condition where the placenta grows into the uterine wall in varying degrees, PAS occurs in 0.01-1% with a pooled prevalence of 0.17% of deliveries or 1-2% of PPH but is rising rapidly. PAS is rare and connected to PP, 70-90% of cases of PAS represent a low-lying PP. Placenta accreta, increta and percreta constitute increasingly perilous conditions and although rare they account for 25-30% of PPH cases that result in hysterectomy. PP and PAS are rising and iatrogenic of origin, they usually occur due to previous scarring of the uterine wall after cesarean section, due to remnants after the use of topical hemostatics or after other instrumentalizations of the endometrium within the uterus including hysteroscopy, IVF, abortion and malformations.

Separation of the placenta from the decidua and the following haemostasis at the placenta site is a challenge since the maternal blood flow must diminish from 500-800 ml/min to zero within a few minutes. This happens due to 1) immense contractions of the uterine muscle compressing the spiral arteries and concomitantly diminishing the size of the placenta site 10-fold and 2) a local activation of the fast extrinsic coagulation system. The effect of topical rFVIIa upon the hemorrhaging placenta site has been tested in a small PoC study. 5 patients underwent cesarean section for PP, 2 of them had in addition PAS. After delivery of the child and the placenta, only 2 minutes of exposure of 1 mg rFVIIa in a saline solution of 250 mL shoved visibly remarkable haemostasis at the placenta site. There were no adverse effects, no over spill of rFVIIa to the systemic circulation, and no thrombotic events (Schjoldager et al, AJOG 216; 608.e1-5).

The state-of-the-art treatment of PPH in high income countries treatment includes multidisciplinary treatment involving medical, mechanical, and surgical means:

PPH>500 mL: First-line therapies: Uterotonics and infusions of liquids, controlled cord traction (CCT) and uterine massage.

After delivery of the placenta, bladder catheterization, bimanual uterine compression, inspection and palpation in adequate anesthesia, suture of tears, removal of retained placenta elements.

PPH>1000 mL: Second-line therapies: Tamponade with Bakri balloon/rolled gauze, full blood and blood products. Uterine compression suture (B-Lynch), ligation of the uterine artery, ligation of the internet iliac artery, uterine artery embolization, peripartum hysterectomy.

In low-income countries many of these procedures and medications are not available.

U.S. Pat. No. 8,461,115 and EP 2004214 describe methods for treatment of intrauterine hemorrhages-selected from the group consisting of postpartum hemorrhage and cesarean section, persistent and recurrent hemorrhage such as hemorrhage due to uterine fibroids or other uterine neoplasia— with Factor FVII and biological active variants thereof. These patent documents do not distinguish between hemorrhages secondary to atony, trauma, PP/PAS or coagulative disorders and do not in detail describe the methods, i.e., narrowly define dosing, the pharmaceutical composition, positioning or duration of the treatments. Thus, there is a need in the field for improved treatments of hemorrhages which can be readily applied without unacceptable risk of thrombosis.

SUMMARY

The present invention is based on the surprising finding that placing rFVIIa directly at the hemorrhaging placenta site postpartum by the use of a dual functioning carrier/barrier in the form of a tamponade with a medical dressing, such as a rolled gauze, can inhibit or even stop the hemorrhage—for example in an effective amount and concentration in a suitable solution, in a pharmacological composition with a carrier that leaves no remnants, and for a predefined amount of time which is enough but not too long, such that hemorrhage can be inhibited without increasing risk of thrombosis in the patient and even without increased risk of forming bacterial infections. This invention is further based upon finding that the organism's highest concentration of tissue factor (TF) is present at the maternal site of the placenta site i.e., at the surface of the vast amounts of decidua cells present in the Nitabuch Layer, the exact separation site for between uterus and placenta upon expulsion of placenta after birth. FVIIa, when presented together with a suitable carrier to keep FVIIa at the hemorrhage site will—mimicking the physiologic hemostasis—through complexing with TF, accelerate the basic coagulation $10^6$-fold with no need of addition of other coagulation factors. The invention is capable of treating all hemorrhages from the placenta site. The positioning of the treatment is carefully chosen. In some embodiments, as soon as PPH>500 mL is discovered, inspection and palpation are swiftly made, trauma treated by suturing and retained tissue removed to ensure that the hemorrhage source is the placenta site. The uterus is quickly packed with a 4 m sterile, rolled gauze soaked in a FVIIa/saline solution composition at a concentration that leads to efficacy with no adverse effects. In the case of atony, uterotonics infusions are stopped. The tamponade is kept for 4-6 hours up to 24 hours. Which allows internalized oxytocin receptors to reappear at the surface of the muscle cell membranes and the uterine muscle to regain its strength. No adverse effects have been registered with no FVIIa entering the systemic circulation.

In one aspect, a method is provided for the treatment or amelioration of postpartum haemorrhage (PPH) from a uterus having a non-open corpus in a female subject, comprising the consecutive steps of:

a. providing a medical dressing suitable for uterine insertion to form a tamponade, wherein the medical dressing is soaked or smeared in a composition comprising from 1 mg to 12 mg of activated Factor VII (FVIIa) polypeptide or a pharmaceutically acceptable variant or prodrug thereof,
b. inserting the medical dressing into the female subject's uterus such as to form a tamponade, and
c. maintaining the medical dressing in the uterus for at least 15 minutes, thereby treating or ameliorating the postpartum haemorrhage.

Further, in one aspect the present disclosure provides a method for diagnosis of PPH in a female subject and subsequent treatment of PPH, comprising the steps of:

a. Determining if the subject has lost 500 mL blood or more from the subject's uterus subsequent to giving birth,
b. Wherein if the subject has lost 500 mL blood or more, PPH is diagnosed, and
c. a medical dressing suitable for uterine insertion to form a tamponade soaked or smeared in a composition comprising from 1 mg to 12 mg of an activated Factor VII (FVIIa) polypeptide or a pharmaceutically acceptable variant or prodrug thereof, is inserted into the female subject's uterus such as to form a tamponade, and
d. the medical dressing is maintained in the uterus for at least 15 minutes, thereby treating the postpartum haemorrhage.

Further, in one aspect, a composition is provided comprising from 1 mg to 12 mg of an activated Factor VII (FVIIa) polypeptide or a pharmaceutically acceptable variant or prodrug thereof, such as from 1 mg to 11 mg, such as from 1 mg to 10 mg, such as from 2 mg to 9 mg, such as from 3 mg to 8 mg, such as from 4 mg to 7 mg, such as from 5 mg to 6 mg.

In a further aspect, a solution is provided comprising the composition as defined herein, wherein the concentration of FVIIa is at least 1 mg/250 mL.

In a further aspect, a haemorrhage inhibiting patch is provided comprising a carrier soaked in the solution as defined herein, and/or smeared in the composition as defined herein.

In a further aspect, a composition as defined herein is provided for use in the treatment, prevention, or ameliorating of haemorrhage in a subject.

In a further aspect, the solution as defined herein is provided for use in the treatment, prevention, or ameliorating of haemorrhage in a subject.

In a further aspect, the haemorrhage inhibiting patch as defined herein is provided for use in the treatment, prevention, or ameliorating of haemorrhage in a subject.

In a further aspect, a composition comprising from 2 mg to 10 mg of a FVIIa polypeptide or a pharmaceutically acceptable variant or prodrug thereof for use in the treatment of postpartum haemorrhage in a subject is provided, wherein the composition is administered directly at the site of haemorrhage at the placenta site in the subject and wherein the composition is maintained in contact with placenta site for from 2 minutes to 7 hours.

In a further aspect, a method for diagnosis of PPH in a subject and subsequent treatment of PPH is provided, comprising the steps of:

a. Determining if the subject has lost 500 mL blood or more from the subject's uterus subsequent to giving birth,
b. Wherein the subject has lost 500 mL blood or more, PPH is diagnosed and the composition, the solution, and/or the haemorrhage inhibiting patch as defined herein is administered to the subject.

In a further aspect, a kit of parts is provided comprising: an activated Factor VII (FVIIa) polypeptide or a pharmaceutically acceptable variant or prodrug thereof, saline, and a gauze suitable for vaginal insertion to form a tamponade, and optionally instructions for use.

DESCRIPTION OF DRAWINGS AND FIGURES

The figures included herein are illustrative and simplified for clarity, and they merely show details which are essential to the understanding of the invention, while other details may have been left out. The figures and drawing included herein are:

FIG. 1 shows [The state-of-the-art treatment of PPH with the positioning of the topical rFVIIa/rolled gauze method. Numbers in EU, early onset of the treatment:

A time axis goes from top to bottom.

The central column shows blood loss with time and the estimated numbers of patients with PPH.

The left big arrow marks the timing of inspection/palpation of the vulva, vagina, cervix and uterus for the diagnostics and subsequent treatments, left column.

The smaller tiny arrows show in which cases the topical treatment/tamponade is applicable.

The right big arrows show the timing of the first-line therapies, rolled gauze and the Bakri balloon, and the second-line treatments, therapies shown in the right column.

The black horizontal line marks the distinction between the less harmful and the invasive treatments of PPH.]]

Figure 2:
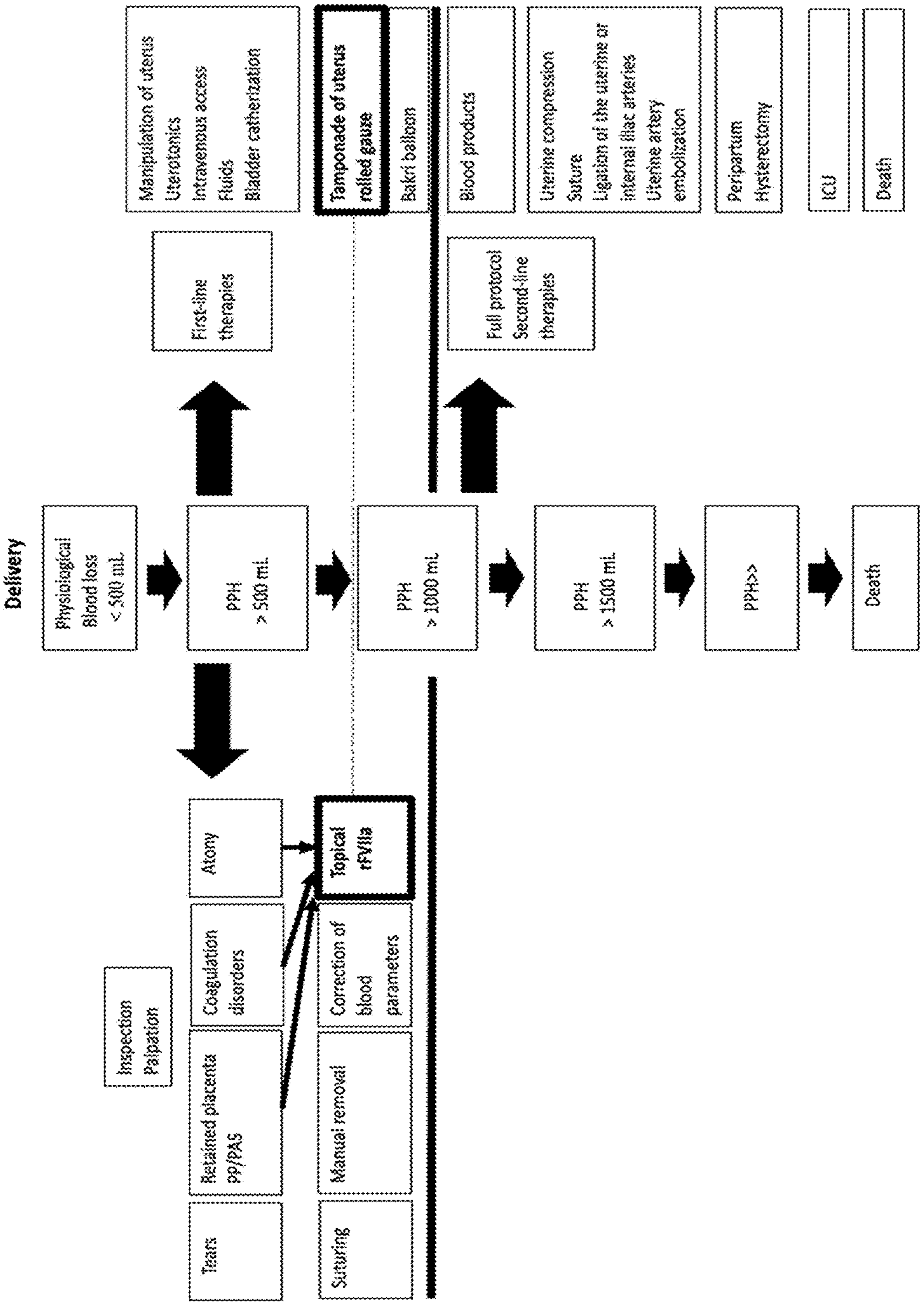

FIG. 2 shows a simplification of FIG. 1. [The state-of-the-art treatment of PPH with the positioning of the topical rFVIIa/rolled gauze method. A time axis goes from top to bottom.

The central column shows blood loss with time.

The left big arrow marks the timing of inspection/palpation of the vulva, vagina, cervix and uterus for the diagnostics and subsequent treatments, left column.

The smaller arrows show in which cases the topical treatment/tamponade is applicable.

The right big arrows mark when to begin the first-line therapies, rolled gauze and the Bakri balloon, and when to apply the second-line treatments, therapies shown in the right column.

The black horizontal line marks the distinction between the less harmful and the invasive treatments of PPH.]

INCORPORATION BY REFERENCE

All publications, patents, and patent applications referred to herein are incorporated by reference to the same extent as if each individual publication, patent, or patent application was specifically and individually indicated to be incorporated by reference. In the event of a conflict between a term herein and a term in an incorporated reference, the term herein prevails and controls.

DETAILED DESCRIPTION

Definitions

The present section contains a set of definitions which can be used along with common general knowledge to assist the interpretation of particular features of the present disclosure.

In the context of the present disclosure, "biocompatible" or "biocompatibility" refers to the ability of a material, such as a carrier to function in vivo, such as in or on a subject without eliciting detrimental local or systemic responses in the subject. A "biocompatible" carrier according to the present disclosure should further be usable in treatment of hemorrhage e.g. for a predefined amount of time, e.g. for an amount of time sufficient to achieve haemostasis and at most 6 hours to avoid infection risk, such as from 1 to 24 hours, such as from 4 to 6 hours and subsequently be removable from the site of hemorrhage or close proximity to the site leaving no trace material that pose a health risk to the subject.

The term "tear resistance" refers to the resistance of a material, such a carrier toward tearing during use. This property is controlled by the chemical composition as well as the physical construction of the material.

The term "a non-open uterine corpus" refers to the condition of the uterus after vaginal delivery or cesarean delivery following closure of the uterotomy.

The term "wear resistance" refers to the resistance of a material, such a carrier toward wearing during use. This property is controlled by the chemical composition as well as the physical construction of the material. Wear resistance generally refers to the material's ability to resist material loss by mechanical action, such as rolling, twisting, and/or folding.

The term "medical dressing" as used herein refers to a sterile pad or compress used to cover and protect a wound while promoting healing. The term "medical dressing suitable for uterine insertion to form a tamponade" or "medical dressing in the form of a tamponade suitable for uterine insertion" as used herein refers to a medical dressing according to the present definition which is of a particular size such that it can be packed into the uterus to create a mechanical barrier optionally using only the subject's anatomy to stop the bleeding and/or provide enough compressive force keeping it in place, i.e. as a tamponade to stop the bleeding.

The term "gauze" herein refers to a woven or non woven sterile cotton item. If made of 100% cotton, cotton gauze fabric is hypoallergenic, non adhesive and is not irritating the wound. Woven gauze has a loose open weave. The loose nature allows the solution or composition comprising rFVIIa to be absorbed into the fibers, and subsequently being desorbed upon receiving a mechanical stimulus, such as squeezing of the gauze during the process of packing the uterus. Similarly, the loose nature allows fluids from the bleeding placenta site to be absorbed into the fibers. Non woven gauze is made from fibers that resemble a weave. But they are not, they are pressed together and condensed. This tight pattern helps non woven fibers to absorb even more fluid. The non woven gauze can for example be made of cotton, rayon or polyester.

The term "rolled gauze" as used herein is a layered, woven cotton medical bandage but also a medical dressing. It is a long strip of non-stretchy gauze rolled into a convenient easy-to-apply cylinder that makes it simple to wrap. It is required for wounds that require compression. Despite not being designed for the highest absorbency, gauze rolls can be used to pack large wounds and cavities to slow bleeding and prevent blood from pooling inside the cavity. It is suitable for uterine insertion to make a tamponade and thus functions dually as a mechanical barrier and a carrier.

The term "amelioration" is used interchangeably herein with "treatment" and refers to the act of making a condition, such a pathological condition, such as haemorrhage better, i.e. less dangerous for the subject suffering from the condition.

The term "prodrug" as used herein refers to a molecule that can undergo degradation, such as hydrolytic degradation to form a bioactive compound. In the case the bioactive compound is FVIIa, a non-limiting example of a prodrug of FVIIa can undergo hydrolysis under physiological conditions to provide FVIIa.

Active management of third stage: consists of interventions designed to facilitate the delivery of the placenta to diminish the risk of PPH. Involves 3 components: Administration of an uterotonic, controlled cord traction (CCT) for the delivery of the placenta and massage of the uterine fundus.

The term “amnion” as used herein means the innermost of the amniotic membranes of the amniotic sac, avascular.

The term “chorion” as used herein means the outermost membrane of the amniotic sac, providing nutrition to the amnion membrane and forming chorionic villi in the placenta.

The term “amniotic sac” as used herein means the sac within the embryo and later foetus. It contains amniotic fluid that acts as a cushion to protect the developing foetus. The amniotic fluid contains the body’s highest amount of tissue factor as an extra haemostatic protection in case of lesions of the amniotic membranes.

The term “atony” as used herein means lack of physiological tone of a contractile organ.

The term “blood clot” as used herein means the outcome of the blood coagulation cascade, formed by conversion of soluble plasma fibrinogen into insoluble fibrin. The blood clot physically stops the haemorrhage and forms the matrix for following wound healing.

The term “blood coagulation” refers to the action of a blood changing to a solid or semi-solid state. In the intrinsic pathway to coagulation a trauma happens inside the vascular system and involves the factors XII to be converted to XIIa, XI to XIa and IX to IXa, X to Xa, prothrombin to thrombin, fibrinogen to soluble fibrin, and to solid fibrin by XIIIa.

In the extrinsic pathway a trauma external to the vascular system involves tissue factor and VIIa/VII, converting X to Xa, prothrombin to thrombin, fibrinogen to soluble fibrin, to solid fibrin by XIIIa.

The term “chorioamnionitis” as used herein refers to bacterial infection of the chorion and amnion (the membranes that surround the foetus). This can lead to infections in both mother and foetus.

The term “haemostasis” as used herein refers to blockage of haemorrhage.

The term “haemostatic” as used herein refers to an agent that shortens the clotting time of blood.

The term “hemorrhage inhibiting composition” as used herein refers to a composition that contains a haemostatic agent. A hemorrhage inhibiting medical dressing is a medical dressing which has a hemostatic effect additionally due to the presence of a hemorrhage inhibiting composition.

The term “hypovolemic shock” as used herein refers to an emergency condition in which severe blood (or fluid) loss makes the heart unable to pump enough blood to the body.

The term “macrosomia” as used herein refers to a newborn with an excessive birth weight.

The term “physiological” as used herein refers to normal functioning of a subject or the subject’s body parts.

The term “placenta” as used herein refers to a temporal organ that develops from the pregnancy in the uterus. It is attached to the inner wall of the uterus, the endometrium and through the umbilical cord the foetus. Maternal blood circulates in one part of the placenta, foetal blood circulates in chorionic villi that are embedded in the maternal pool of blood and their surface maximises the area for contact with the maternal blood. Here foetal/maternal exchange of nutrients-oxygen and waste-carbon dioxide to/from the foetus occurs. When the child is born, the umbilical cord collapses, the placenta shrinks and is shredded off by contractions of the uterus.

The term “placenta accreta spectrum (PAS)” as used herein refers to a situation where the placenta grows into the uterine wall in varying degrees.

The term “placenta accreta” as used herein refers to a situation where the placenta villi adhere directly to the myometrium with no decidual interface.

The term “placenta increta” as used herein refers to a situation where the placental villi invade the myometrium.

The term “placenta percreta” as used herein refers to a situation where the villi invade and penetrate the full thickness of the uterine wall including the serosa. Placenta percreta can invade intra-abdominal tissues, organs and vessels.

The term “placenta previa (PP)” as used herein refers to a condition in which the placenta is implanted so that the internal orifice of the cervix is covered, thus hindering a normal delivery of the child.

The term “preeclampsia” as used herein refers to a serious blood pressure condition that develops during pregnancy after week 20. Cardinal symptoms are hypertension, proteinuria, oedema.

The term “postpartum haemorrhage (PPH)” as used herein refers to abnormal haemorrhage >500 mL within 24 hours after delivery of the child.

The term “topical administration” as used herein refers to the administration of an active agent to the surface of the skin or any other body part, such as at the mucous membrane of the eye, ear, nose, mouth, vulva, vagina, cervix, uterus or at the placenta site with the intent of containing the pharmacological effect of the agent primarily to the surface or mostly within the outer layers of the body part, such as skin or mucous membrane.

The term “uterotonic” as used herein refers to a substance that stimulates muscular tone in the uterus.

The term “Intrauterine haemorrhage” as used herein refers to a haemorrhage which happens in the uterus and differs from other types of haemorrhage. This is due to the vascular physiology found in the uterus. Contrary to other parts of the body, the uterus comprises spiral arteries that are tightly coiled. These are remodeled during pregnancy to become more rigid and increase in diameter to ensure extensive blood supply to the placenta. This influences the nature of intrauterine haemorrhage, because the physiological structure of these arteries increases the risk of profuse haemorrhages and loss of large volumes of blood. Also, the haemorrhage area of postpartum haemorrhage is large due to the attachment site of the placenta.

FVIIa Polypeptide

In some embodiments, recombinant FVIIa (rFVIIa) is to be used in a haemostatic effective manner against postpartum haemorrhages from the placenta site. In the context of the present disclosure, a haemostatic effective manner refers to a setting where e.g. rFVIIa is used with an early onset of an optimised encounter with TF, with a carrier that brings rFVIIa in close contact with TF at the placenta site leaving no traces and, in an amount, and concentration that persist for enough time to hamper the haemorrhage and for short enough time to not cause infection. The positioning of rFVIIa, the choice of carrier, the dose, the duration of treatment gives each significant input to a haemostatic effective treatment of PPH caused by haemorrhages from the placenta site i.e., uterotonic resistant atony, PP/PAS as well as haemorrhages due to coagulative disorders.

The complete nucleotide and amino acid sequences for human Factor VII are known, U.S. Pat. No. 4,784,950 (wild type Factor VII). When used herein, the term Factor VII or FVII is intended to compass wild-type factor VII as well as variants of Factor VII exhibiting the same, modified or improved biological activity to wild type Factor VII, Factor VII polypeptides in their uncleaved (zymogen) form, as well as those that have been proteolytically processed to yield their respective bioactive forms, designated FVIIa, including Factor VII/activated Factor VII/Factor VIIa/FVIIa/and recombinant forms of Factor VII, rFVII, recombinant, activated Factor VI/rFVIIa in various glycoforms as for example disclosed in EP Patent No. 2 262 330 A1.

Factor VII (former known as proconvertin), a serine protease, is the only coagulation factor that can circulate in the blood not only in its zymogen form FVII (99%), both also in its active form, FVIIa (1%) without triggering the coagulation cascade, since its cofactor Tissue factor (TF) is positioned outside the bloodstream on the surface of perivascular cells and epithelial cells at organs and body surfaces.

In one embodiment, a FVIIa polypeptide or the pharmaceutically acceptable variant or prodrug thereof is used in the context of the present disclosure. In some embodiments, the FVIIa polypeptide or the pharmaceutically acceptable variant or prodrug thereof is selected from the group consisting of: recombinant FVIIa (rFVIIa), a glycoform thereof, wild type FVIIa, and a factor VII polypeptide in uncleaved form (zymogen).

In one embodiment, the FVIIa polypeptide or the pharmaceutically acceptable variant or prodrug thereof has at least 60% sequence identity to the amino acid sequence for the human FVIIa, as known in the art, such as at least 65% sequence identity, such as at least 70% sequence identity, such as at least 75% sequence identity, such as at least 80% sequence identity, such as at least 85% sequence identity, such as at least 90% sequence identity, such as at least 92% sequence identity, such as at least 94% sequence identity, such as at least 96% sequence identity, such as at least 98% sequence identity such as at least 99% sequence identity.

Genetic recombinant Factor Vila, rFVIIa, has been approved by FDA:

- Eptacog alfa: NovoSeven, NOVO A/S, Bagsvaerd, Denmark is recombinant, activated Factor VII made from transgenic hamster kidney cells. AryoSeven, from AryoGen Pharmed from Iran is a biosimilar.
- Eptacog beta: SevenFact, see U.S. Pat. No. 9,029,316B2 is made by LFB Laboratories, Les Ulis, France is recombinant, activated Factor VII made from transgenic rabbit mamma gland cells. This rFVIIa is N- and O-glycosylated slightly different from NovoSeven which may enhance haemostasis even more. Coagil-VII from Generium Pharmaceuticals, Russia, is distributed via Stragen, Switzerland.

To mention, but not to exclude other formulations of FVIIa available now or in future, a rFVIIa could also be used from insects or other bacteria. This is cheaper to make and is less glycosylated.

TF exerts its cofactor effects from two sources: 1) TF is omnipresent in subendothelial cells surrounding the vessels and in organ capsules and thereby forms a "haemostatic envelope". 2) Additionally, TF is highly expressed in a tissue specific manner in vital organs: Brain (in the astrocytes), lungs (in the alveolar cells) and uterus (in the decidual stromal cells), serving as an extra haemostatic protection. From the moment the placenta starts to be detached from the uterus wall—excessively concentrations of uterine TF denude, further the amniotic fluid contains the body's highest concentration of soluble TF (sTF).

The placenta is attached to the (maternal) decidual lining. The basal decidual lining contains an abundance of TF produced by and attached to the decidual stromal cell membranes. The decidual cells are mainly positioned in the Nitabuch layer of the basal lining. This fibrinoid layer is located between the zona spongiosa and zona compacta. This region is the utero-placental boundary layer, the separation layer for placenta. Here the highest tissue-specific expression of TF is found.

The remarkable high concentration of TF at the placenta site marks a principle of treatment for topical FVIIa against PPH, see U.S. Pat. No. 8,461,115 B2 and EP2004214 B1.

After delivery of the child, the foetal blood to the placenta diminishes and pulsation stops within 2-4 minutes. The placenta shrinks, it is very soft tissue, with a Shear Wave Velocity of 0.983 m/s, much lower than the stiffer endometrium, 2.05 m/s and the uterine myometrium, 2.82 m/s and its separation from the decidua lining begins with the first contraction after birth, thereby exposing huge amounts of TF to the uteroplacental circulation.

Compositions

In some embodiments, a composition is provided which is a haemorrhage inhibiting composition. The composition is haemostatic as it contains a FVIIa polypeptide as defined herein. The composition optionally contains one or more pharmaceutically acceptable carriers.

Solutions

In some embodiments, a solution is provided comprising the composition as herein wherein the concentration of FVIIa is at least 1 mg/250 mL.

In some embodiments, the solution further comprises one or more pharmaceutically acceptable excipients. In one embodiment, the one or more pharmaceutically acceptable excipients are selected from NaCl, histidine, methionine, calcium chloride dihydrate, polysorbate 80, hydrochloric acid and sodium hydroxide (for pH adjustments) and one or more polysaccharides.

In some embodiments, the solution comprises a physiologically acceptable buffer. The buffer may be any acceptable buffer known in the pharmaceutical arts being physiological compatible. In addition, a buffer may additionally act as a stabiliser, for example, as an antioxidant which does not reduce a disulfide bond. In one embodiment, the buffer comprises an ascorbate, sorbate, formate, lactate, fumarate, tartrate, glutamate, acetate, citrate, gluconate, histidine, malate, phosphate or succinate buffer. In another embodiment, the buffer comprises an ascorbate, lactate, tartrate, citrate, gluconate, malate, isocitrate or 2-hydroxybutyrate buffer.

In one embodiment, the solution comprises one or more polysaccharides, such as starch.

In one embodiment, the solution comprises:

a. 2 mg FVIIa,
b. histidine
c. NaCl, and
d. about 500 mL Water.

Hemorrhage Inhibiting Medical Dressing

The present disclosure provides a medical dressing which can be soaked or smeared in a composition as disclosed herein to provide a hemorrhage inhibiting medical dressing.

In one embodiment, a method is provided for the treatment or amelioration of postpartum haemorrhage (PPH) from a uterus having a non-open corpus in a female subject, comprising the consecutive steps of:

a. providing a medical dressing suitable for uterine insertion to form a tamponade, wherein the medical dressing is soaked or smeared in a composition comprising from 1 mg to 12 mg of activated Factor VII (FVIIa) polypeptide or a pharmaceutically acceptable variant or prodrug thereof,
b. inserting the medical dressing into the female subject's uterus such as to form a tamponade, and
c. maintaining the medical dressing in the uterus for at least 15 minutes, thereby treating or ameliorating the postpartum haemorrhage.

In one embodiment, a haemorrhage inhibiting patch is provided comprising a carrier soaked in the solution as defined herein, and/or smeared in the composition as defined herein. In one embodiment, a hemorrhage inhibiting medical dressing is provided comprising a dual working barrier/carrier soaked in the solution as defined herein, and/or smeared in the composition as defined herein.

In some embodiments, the haemorrhage inhibiting patch comprises a medical dressing. In some embodiments, the haemorrhage inhibiting patch comprises a gauze suitable for vaginal insertion to form a tamponade. In some embodiments, the haemorrhage inhibiting patch comprises a pH neutral gauze, or a pH neutral swab, for example wherein the pH neutral gauze is a pH neutral 5 or 10 m gauze.

Barriers

In some embodiments, the hemorrhage inhibiting medical dressing has to withstand heavy bleedings from an up to 20 cm in diameter placenta site.

In some embodiments, the medical dressing is configured for absorbing the composition as defined herein at a first time point and releasing the composition at a second time point subsequent to the first time point by a mechanical stimulus.

In some embodiments, the medical dressing is hypoallergenic, non-adhesive and non-irritating to a wound.

In some embodiments, wherein the medical dressing is a gauze.

In some embodiments, the medical dressing is rolled, packed, twisted or folded prior to or during step b of the present method to provide the tamponade.

In some embodiments, the hemorrhage inhibiting medical dressing comprises a gauze suitable for uterine insertion to form a tamponade. In some embodiments, the hemorrhage inhibiting medical dressing comprises a rolled gauze. for example wherein the gauze is a 4 or 10 m gauze. A rolled gauze changes its dimensions through the packing of the uterus from flat to a handball-sized, such as a uterine-sized firm barrier that opposes blood otherwise escaping from the placenta site. A rolled gauze is non-adhesive and thereby not irritating the surrounding mucosa and no remnant is left upon retrieval. In some embodiments, the medical dressing changes its dimensions through the packing of the uterus from flat to uterine-sized during insertion forming a tamponade.

Carriers

In some embodiments, the carrier for the FVII polypeptide defined herein should be a carrier that has its topological agent only loosely attached, not fixed. The carrier can be separated from the hemorrhage site after the bleeding has stopped leaving no remnants or residue behind or leaving only remnants or residue behind which is metabolized or otherwise degraded and discarded by the human or animal body. In the context of the present disclosure, a biocompatible carrier leaves no remnants behind after being used. Thus, preferred carriers of the present disclosure are biocompatible.

In some embodiments, the carrier is wear resistant and/or tear resistant.

In some embodiments, the carrier is configured for absorbing the composition as defined herein at a first time point and releasing the composition at a second time point subsequent to the first time point.

In some embodiments, the release is inducible by mechanical stress, such as by folding, twisting, and/or folding of the carrier.

In some embodiments, the carrier is a porous and flexible material. These features configure the carrier for absorbing the composition and/or solution, and for being flexible enough such that the carrier can be placed in contact with or in close proximity to the placenta site where the composition and/or solution is released.

Smaller bleedings are typically treated in surgery with small patches such as gelatine of oxidized regenerated cellulose (ORC) and fibrin sealants that in addition contain a fixed topical agent such as thrombin. These hemostatics can be used in open surgery and have previously been described to successfully inhibit smaller bleedings when placed at the wound and held manually for 3 minutes or more to fixate the haemostatic which is then left in situ for later absorption, which may take longer that the described up to 8-13 weeks. Infections, immunological reactions, giant cell granuloma and permanent scarring of the uteruine lining have been described. These hemostatics have no use in PPH where 1) the profuse bleeding will push off the patch if not firmly held in constant contact; 2) the source of the bleedings, the placenta site is not visible after vaginal delivery or after cesarean delivery with a closed uterotomy; 3) remnants leading to infections and immunological reactions with risks of scarring are often described after the use of these haemostatics (Topical hemostatic agents at time of obstetric and gynecological surgery, ACOG committee opinion, Obstetrics and Gynecology 136; 4: e 81-e88, 2020, US 2004/106344, WO 90/13320). Since the uterine mucosa is especially vulnerable to any remnants because they augment the risk of scarring and thereby of the very dangerous PP/PAS in later pregnancies—these hemostatics have no place in the treatment of PPH.

In some embodiments, for smaller bleedings, a pH neutral swab soaked in rFVIIa and saline is a preferred carrier for treatment of PP/PAS during cesarean section. Many carriers span from collagen, gelatine, polysaccharides, chelating agents to carriers with coagulative active agents such as thrombin and fibrinogen. Some are based on nonhuman tissue and blood derived agents, which heightens the risk of immunological reactions and infections in the uterus. Therefore in some embodiments, a pH-neutral rolled gauze soaked in a rFVIIa/saline solution is a perfect carrier against PPH both after vaginal and cesarean delivery with closed uterotomy. Rolled gauze alone used as used in the present context has a success rate of close to 80% in acting as a mechanical barrier against PPH, and the addition of a composition comprising rFVIIa as disclosed herein augments this tremendously.

Indications

In some embodiments, the present disclosure provides for the treatment, prevention, or ameliorating of haemorrhage in a subject using the composition, solution or haemorrhage inhibiting patch as defined herein.

In some embodiments, the present disclosure provides for the treatment, prevention, or ameliorating of haemorrhage in a subject using the composition, solution or haemorrhage inhibiting medical dressing as defined herein. In the following section, each and every embodiment pertaining to a particular aspect of use can be employed using either the composition, the solution, or the haemorrhage inhibiting medical dressing as defined herein.

In some embodiments, the subject is a human or a non-human subject. In some embodiments, the human subject is female. In some embodiments, the female is puerperal. In some embodiments, the subject is a human subject. In some embodiments, the subject is an animal subject.

In some embodiments, the haemorrhage results from postpartum haemorrhage.

In some embodiments, the condition is postpartum haemorrhage. In some embodiments, the condition is postpartum haemorrhage associated with or resulting from the placenta site.

In some embodiments, the indication for topical use of rFVIIa is PPH haemorrhages from the placenta site. In the context of the present disclosure, the rule of thumb is: Tonus, Trauma, tissue, thrombin, gives the causes and order of importance. Tonus, lack of tonus, atony is caused by an exhausted uterus exposed too much/long time to either endogenous or exogenous oxytocin, the receptors have internalised and will not return to the surface for another 3 hours. Blood is pouring out from an excessively large placenta site. The aim of treatment is to stop exogenous oxytocin and to make haemostasis at the source by topical rFVIIa-TF complexing at the placenta site and to continue the therapy until the uterine muscle regain its force, in some embodiments for 6 hours. In some embodiments, the composition, solution or haemorrhage inhibiting patch is administered topically to the subject at the site of the haemorrhage. In some embodiments, the composition, solution or haemorrhage inhibiting patch is administered topically to the subject's placenta site.

Trauma to the birth canal during the delivery usually involves the cervix and the vagina. Tears are sutured after inspection. No indication for topical rFVIIa. Hence, in some embodiments, the condition is postpartum haemorrhage not associated with or resulting from a trauma, such as a cervical and/or a vaginal trauma.

In some embodiments, the condition is postpartum haemorrhage where one or more uterotonics have been insufficient to cause haemostasis.

In some embodiments, the condition is postpartum haemorrhage associated with or resulting from global or local atony. In some embodiments, the condition is postpartum haemorrhage associated with or resulting from uterotonic resistant global or local atony.

In some embodiments, the condition is postpartum haemorrhage associated with placenta previa (PP) and/or placenta accreta spectrum (PAS).

Tissue is retained either because of atony or because of PP/PAS or left membranes. Through palpation, tissue and membranes are removed. In case of PAS parts of placenta cannot be removed and haemorrhage continues from the placenta site. In some embodiments, the treatment comprises topical treatment with rFVIIa-soaked rolled gauze for 6 hours and exogenous oxytocin to maintain a contracted uterus. In some embodiments, the PAS is characterised by placenta accreta, placenta increta, or placenta percreta.

In some embodiments when PP/PAS are treated during cesarean section, the placenta site can be visualized and sometimes treatment with a rFVIIa-soaked swab for some minutes is sufficient to obtain hemostasis, if not, a rFVIIa-soaked rolled gauze should be placed for 6-24 hours.

In some embodiments, such as in the rare case of retained placenta parts after vaginal delivery, topical rFVIIa-soaked rolled gauze treatment is installed for 6-24 hours after palpation. Additionally, an antibiotic treatment is installed when the tamponade is kept beyond 6 hours.

In some embodiments, the subject suffers from PPH associated with PP and/or PAS and a composition, solution or hemorrhage inhibiting medical dressing in the form of a soaked swab can successfully be placed in contact with the site of the hemorrhage at a predetermined amount of time, optionally for from 2 minutes to 4 minutes, such as to ameliorate the hemorrhage as earlier described in a small PoC to determine effect and safety (Schjoldager et al, AJOG; 608, e1-e5, 2017).

In some embodiments, the composition, solution, or hemorrhage inhibiting medical dressing, a rolled gauze is placed in close proximity or contact with the site of the hemorrhage for from 6-24 hours. Additionally, an antibiotic treatment is installed when the tamponade is kept beyond 6 hours.

In some embodiments, in the cases of general atony—which account for 75% of PPH cases or 94% of PPH non-involving trauma to the vulva/vagina/cervix—the predefined amount of time is chosen such that the composition is kept long enough close to the site of hemorrhage to ameliorate the hemorrhage while avoiding prolonged contact such that the infection risk increases significantly, which is around 6 hours. The present disclosure surprisingly reaches after the predefined amount of time a satisfying amelioration of the hemorrhage before the infection risk significantly increases. The predefined amount of time is in some embodiments an amount of time which is at most 7 hours, such as at most 6 hours. The predefined amount of time in some embodiments is an amount of time sufficient to achieve haemostasis. The predefined amount of time in some embodiments is an amount of time sufficient to achieve haemostasis and at most 7 hours.

Additionally, an antibiotic treatment is installed when the tamponade is kept beyond 6 hours.

In some embodiments, the predefined amount of time is at most 7 hours, such as from 2 minutes to 7 hours, such as from 2 minutes to 4 minutes, such as from 4 minutes to 30 minutes, such as from 30 minutes to 1 hour, such as from 1.0 hours to 1.5 hours, such as 1.5 hours to 2.0 hours, such as from 2.0 hours to 2.5 hours, such as from 2.5 hours to 3.0 hours, such as from 3.0 hours to 3.5 hours, such as from 3.5 hours to 4.0 hours, such as from 4.0 hours to 4.5 hours, such as from 4.5 hours to 5.0 hours, such as from 5.0 hours to 5.5 hours, such as from 5.5 hours to 6.0 hours, such as from 6.0 hours to 6.5 hours, such as from 6.5 hours to 7.0 hours.

In some embodiments, the postpartum haemorrhage is associated with or results from the placenta site. In some embodiments, prior treatment of the PPH with one or more uterotonics has been insufficient to cause haemostasis. In some embodiments, the postpartum haemorrhage is associated with or results from global or local atony. In some embodiments, the postpartum haemorrhage is associated with or results from uterotonic resistant global atony and wherein no uterotonics are administered to the subject for at least 4 hours from the medical dressing is inserted in step b of the present method.

Thrombin stands for coagulative disorders. They too result in haemorrhages from the placenta site. A topical treatment is commenced with rFVIIa-soaked rolled gauze at the placenta site for 6 hours, alongside a systemic treatment with correction of the disorder with addition of missing blood components.

In some embodiments, the methods of the present invention are used for the treatment of haemorrhage from the placenta site due to the conditions but not limited to: third trimester premature and mature deliveries with complications such as postpartum haemorrhage, uterine atony, lateral, marginal, partial or total placenta previa, placenta accreta spectrum, retention of cotyledon, coagulative disorders such as but not exclusive: haemolysis, disseminated intravascular coagulation (DIC), fibrinolytic disorders, elevated liver enzymes and low platelets (HELLP) syndrome, hereditary deficiency of blood coagulation factor VII, Glantzmann's thrombasthenia, von Willebrand's disease, Borgschulte-Grigsby combined deficiency of blood coagulation factors II, VII, IX and X.

In some embodiments, the subject undergoing treatment, prevention, or amelioration with the composition, solution, or haemorrhage inhibiting patch suffers from one or more further disorders selected from the group consisting of: DIC, haemolysis, HELLP, and a fibrinogen defect.

Uterine Hemostasis Differs from Haemostatic Events in Other Organs

Two hemostatic mechanisms happen concomitantly after delivery of the child, see FIG. 1:

1) The uterine muscle retracts a unique characteristic of the uterine muscle to maintain its shortened length following each contraction, thereby undermining and shearing off the placenta from the decidua lining, wringing the uterus and compromising the spiral arteries. The placenta site is diminished from 20 cm in diameter 10-fold down to a diameter of 6 cm.
2) A local, remarkable coagulation occurs at the placenta site due to a haemostatic mechanism in the uterine circulation during placental separation resulting in thrombin formation due to local release of/exposure to a thromboplastin-like activity (i.e., TF-like) at the placenta site. A physiological blood loss is 500 mL.

In some embodiments, the subject of the present disclosure has lost 500 mL or more blood from the subject's uterus subsequent to giving birth, such as 600 mL or more, such as 700 mL or more, such as 800 mL or more, such as 900 mL or more, such as 1000 mL or more, such as 1100 mL or more, such as 1200 mL or more, such as 1300 mL or more, such as 1400 mL or more, such as 1500 mL or more, such as 1600 mL or more, such as 1700 mL or more, such as 1800 mL or more, such as 1900 mL or more, such as 2000 mL or more, such as 2100 mL or more, such as 2200 mL or more, such as 2300 mL or more, such as 2400 mL or more, such as 2500 mL or more.

In some embodiments, the subject has lost 1000 mL or more blood from the subject's uterus subsequent to giving birth. In some embodiments, the subject has lost 1500 mL or more blood from the subject's uterus subsequent to giving birth. In some embodiments, the subject has lost 2500 mL or more blood from the subject's uterus subsequent to giving birth.

In some embodiments, a composition, or a solution is provided comprising from 2 mg to 10 mg of a FVIIa polypeptide or a pharmaceutically acceptable variant or prodrug thereof for use in the treatment of postpartum haemorrhage in a subject is provided, wherein the composition is administered directly at the site of haemorrhage at the placenta site in the subject and wherein the composition is maintained in contact with placenta site for from 2 minutes to 7 hours.

In some embodiments, a haemorrhage inhibiting patch is provided comprising a carrier and from 2 mg to 10 mg of a FVIIa polypeptide or a pharmaceutically acceptable variant or prodrug thereof for use in the treatment of postpartum haemorrhage in a subject is provided, wherein the composition is administered directly at the site of haemorrhage at the placenta site in the subject and wherein the composition is maintained in contact with placenta site for from 2 minutes to 7 hours. Separation of the placenta from the decidua lining and the following haemostasis at the placenta site is a challenge since the maternal blood flow must diminish from 500-800 ml/min to zero within a few minutes.

Timing and Positioning

The third phase of delivery is defined as the period after the delivery of the child until the delivery of the placenta. Its duration is normally 6-10 minutes. It can be divided into 3 phases:

1. Latent phase, average duration 101 s, is the time interval between delivery of the foetus and the beginning of placental separation from the decidua. Duration of blood flow between the myometrium and placenta is in average 33 s. Ultrasound reveals that basal blood flow cessation between the placenta and myometrium occurring at the end of the latent phase is the hallmark of normal placental separation. The latent phase is the main determinant of the duration of the third stage of labour, which is unaltered by oxytocin administration.
2. Detachment phase, average 56 s is the period during which the placenta separates from decidua. It begins with the first contraction of the uterus after delivery of the child. This phase can be monophasic or multiphasic. Monophasic placental separation is visualised as a constant shearing off the placenta towards the internal os. Multiphasic placental separation shows pauses between active detachment phases.
3. Expulsion phase, duration 77 s begins with completed separation and ends with the vaginal delivery of the placenta. The third stage duration is average 365 s.
4. PPH (phase 4). Under pathological conditions with PPH that goes beyond phase 3, some define this as phase 4 PPH. PPH emerges in the third phase of delivery or beyond.

Already in 1936 Brandt, using intra-umbilical sodium iodine and X-ray, observed that during normal delivery the placenta was separated and folded in the lower uterine segment within 3 min of delivery. Brandt postulated active management of the third stage of labour after an interval of 10 min instead of 30-60 min, this suggestion is supported by new studies. Hence, active management should be practised immediately with CCT in case of PPH and after 10 min if placenta is not already delivered and not to wait 30 min.

Since PPH occurs in 10% of deliveries and continues into severe PPH in 60-70% of these cases and continuing, time and the amount of haemorrhage are working against saving the mother. For these reasons, the present disclosure determines early positioning of the rFVIIa treatment: When PPH has been detected and first-line therapies are ongoing, the placenta is removed followed by inspection and palpation in adequate anaesthesia to ensure that the haemorrhage source is the placenta site, and immediate installation of the rFVIIa-treatment.

Dosing

The preparations are administered in a manner compatible with the dosage formulation, and in such amounts as will be therapeutically effective. The quantity to be administered depends on the subject to be treated including the weight and age of the subject. In some embodiments, suitable dosage ranges are per kilo body weight normally at the order of several hundred μg active ingredient per administration with a preferred range from 0.1 μg to 10.000 μg per kilo bodyweight. Using monomeric forms of the compounds, the suitable dosages are in some embodiments in the range of 0.1 μg to 5000 μg per kilo bodyweight, such as in the range from 0.1 μg to 1000 μg per kilo bodyweight. Using multi multimeric forms of the compounds, the suitable dosages are in some embodiments in the range of from 0.1 μg to 1000 μg per kilo bodyweight, such as in the range of 0.1 μg to 750 μg per kilo bodyweight, and especially in the range of from 0.1 μg to 500 μg per kilo body weight such as in the range of 0.1 μg to 250 μg per kilo bodyweight.

In one embodiment, a composition is provided comprising from 1 mg to 12 mg of an activated Factor VII (FVIIa) polypeptide or a pharmaceutically acceptable variant or prodrug thereof, such as from 1 mg to 11 mg, such as from 1 mg to 10 mg, such as from 2 mg to 9 mg, such as from 3 mg to 8 mg, such as from 4 mg to 7 mg, such as from 5 mg to 6 mg.

In one embodiment, the composition comprises from 2 mg to 10 mg of the FVIIa polypeptide or the pharmaceutically acceptable variant or prodrug thereof.

Administration may be performed once or may be followed by subsequent administrations.

A preferred dosage for PP/PAS treatment to an open uterus during caesarean section would be from about 0.1 to about 5 mg, preferably from about 0.3 mg to about 3 mg, such as from about 0.5 to about 1.5 mg and especially in the range of 1.0 to 2.0 mg per administration.

A preferred dosage for atony treatment to an intact uterus would be from about 0.1 to about 14 mg, preferably from about 1 mg to about 12 mg, such as from about 5 to about 11 mg and especially in the range of 6 to 10 mg per administration.

In some embodiments, the dosage is from 0.1 mg to 0.5 mg, such as from 0.5 mg to 1.0 mg, such as from 1.0 mg to 1.5 mg, such as from 1.5 mg to 2.0 mg, such as from 2.0 mg to 2.5 mg, such as from 2.5 mg to 3.0 mg, such as from 3.0 mg to 3.5 mg, such as from 3.5 mg to 4.0 mg, such as from 4.0 mg to 4.5 mg, such as from 4.5 mg to 5.0 mg, such as from 5.0 mg to 5.5 mg, such as from 5.5 mg to 6.0 mg, such as from 6.0 mg to 6.5 mg, such as from 6.5 mg to 7.0 mg, such as from 7.0 mg to 7.5 mg, such as from 7.5 mg to 8.0 mg, such as from 8.0 mg to 8.5 mg, such as from 8.5 mg to 9.0 mg, such as from 9.0 mg to 9.5 mg, such as from 9.5 mg to 10.0 mg, such as from 10.0 mg to 10.5 mg, such as from 10.5 mg to 11.0 mg, such as from 11.0 mg to 11.5 mg, such as from 11.5 mg to 12.0 mg.

The dosage of FVIIa polypeptide according to the present disclosure will depend upon the administration to an open uterus during caesarean section for PP/PAS with no atony, dosage typically 2 to 4 mg, or to an intact uterus after VD or CD with closed uterotomy in the case of general atony, dosage typically 6 to 10 mg.

In an open uterus administration, the use of 1 mg NovoSeven in 250 mL of saline solution or 4000 ng/mL has previously been successfully used against PP/PAS. The plasma concentration of FVII is normally 0.5 μg/mL. The plasma concentration of FVIIa is normally 4.3 ng/mL but during pregnancy rises to 12.0 ng/mL or even higher at term. 4000 ng/mL is 4000/12=333 times the physiological plasma concentration at term.

A pregnant woman weighs in average 75 kg and has a 30-50% augmentation of plasma volume to environ 5 L. Systemic rFVIIa, recommended bolus injection for the patient: 90 ⌈g/kg. The amount used for intravenous bolus injection is 90 ⌈g/kg×75 kg=6750 ⌈g resulting in a plasma concentration of 6750 ⌈g/5 L=1350 ⌈g/L or 1350 ng/mL. This is 1350/12=112 times the physiological plasma concentration at term. 4000 ng/mL used against PP/PAS is 3 times higher than the plasma concentration obtained after intravenous administration (4000 ng/mL versus 1350 ng/mL). A certain dilution will probably occur during the application so that the local concentration at the placenta site will be less than applied.

In human studies of local application of rFVIIa, concentrations of rFVIIa have been reported as high as 38 times this concentration without reports of adverse effects (562.5 ⌈g in 3.7 ml=152.000 ng/mL versus 4000 ng/mL, see WO 1993/006855.

For these reasons, and since there is no or barely any risk of overspill of rFVIIa to the systemic circulation, total amounts of use of rFVIIa locally at the placenta site can be up to and even exceed 90 ⌈g/kg corresponding to an use of rFVIIa from 6.750 mg or to 10 mg or even more for a pregnant woman weighing 75 to 100 kg.

In some embodiments, the present invention should preferably exert an effect for hours in the case of global atony. Accordingly, a dose recommended should not exceed 90 ⌈g/kg. In some embodiments, between 2 to 4 mg of rFVIIa in 250 mL of saline is recommended for application to PP/PAS during a caesarean section with an open uterus and complete arrest of haemorrhage, otherwise 6 to 10 mg rFVIIa in 500 mL of saline and a rolled gauze as a carrier, also recommended against global atony. And coagulative disorders.

Duration

Uterine contractions are driven by oxytocin. Oxytocin promotes rhythmic contractions of the uterus by increasing intracellular $Ca^{2+}$ through specific receptors in the myometrium of the uterus. Oxytocin is produced by neurons in the hypothalamus and transported to the posterior pituitary. Pulses of oxytocin are released from the pituitary gland into the circulation with increasing frequency, duration and amplitude from late pregnancy through labour to a maximum of frequencies 3 per 10 min by the end of the second stage of delivery. A four-fold release of oxytocin occurs in connection with birth. During the third stage of delivery oxytocin is released leading to expulsion of the placenta. Oxytocin increases the frequency of existing contractions and raises the tone of the uterine musculature.

Exogenous oxytocin is used 1) antepartum for induction of labour, 2) intrapartum for augmentation of labour, 3) postpartum in the third phase of delivery to facilitate the delivery of placenta and 4) beyond in the fourth phase to diminish PPH. Ironically, PPH is at the same time an indication for and a feared reverse reaction to exogenous oxytocin.

If endogenous or exogenous oxytocin is presented in too high amounts desensitisation of the muscle happens through internalisation of the receptors; the muscle relaxes and remains insensitive to oxytocin for 2-3 hours upon withdrawal of the oxytocin infusion. Atony is the result.

When a uterine tamponade is made with a rolled gauze soaked in a saline solution of rFVIIa due to an atonic uterus, exogenous oxytocin should immediately be stopped. In some embodiments, the duration of the treatment should exceed 3 hours to ensure that the oxytocin receptors have had enough time to re-enter the surface of the myocytes. Therefore, we recommend the tamponade to only be removed after 4, preferably 6 hours. This relatively short period additionally will minimise the risk of infection due to the tamponade.

In some embodiments, the medical dressing is contacted with the site of the haemorrhage for from 4 hours to 24 hours. In some embodiments, the medical dressing is contacted with the site of the haemorrhage for from 6 hours to 24 hours and wherein one or more antibiotics are administered to the female subject.

Combination Treatment

In some embodiments, the composition further comprises, separately or together, one or more additional blood clotting agents and optionally one or more pharmaceutically acceptable carriers.

In some embodiments, the one or more blood clotting agents are selected from the group consisting of: a plasma-derived factor concentrate, a recombinant factor concentrate, emicizumab, desmopressin acetate, epsilon amino caproic acid, and cryoprecipitate.

In some embodiments, the present disclosure provides for treatment with a further haemorrhage inhibiting composition.

In some embodiments, the further haemorrhage inhibiting composition comprises a FVIIa polypeptide selected from the group consisting of: recombinant FVIIa (rFVIIa), a glycoform thereof, wild type FVIIa, and a factor VII polypeptide in uncleaved form (zymogen), preferably wherein the further haemorrhage inhibiting composition comprises recombinant FVIIa (rFVIIa).

In particular embodiments, the further haemorrhage inhibiting composition is administered parenterally. In some embodiments, the further haemorrhage inhibiting composition is administered intravenously.

In some embodiments, the further haemorrhage inhibiting composition is administered intravenously as a bolus or by infusion over a predefined time period.

In some embodiments, the composition, solution, or haemorrhage inhibiting patch is administered topically to the subject at the site of the haemorrhage, optionally to the subject's placenta site, and the further haemorrhage inhibiting composition is administered parenterally, such as intravenously, preferably wherein the further haemorrhage inhibiting composition is administered intravenously as a bolus or by infusion over a predefined time period. Preferably in this setting, the further haemorrhage inhibiting composition is recombinant FVIIa (rFVIIa).

Kit of Parts

In some embodiments, the compounds of the present disclosure are provided in a kit.

PP/PAS Kit contains 2 mg rFVIIa ampul, 2 sterile pH-neutral swabs, 250 mL sterile saline ATONY Kit (60-70 kilo) contains 6 mg rFVIIa ampul, 10 m sterile rolled gauze, 500 mL sterile saline.

ATONY Kit (70-80 kilo) contains 8 mg rFVIIa ampul, 10 m sterile rolled gauze, 500 mL sterile saline.

ATONY Kit (80-100 kilo) contains 10 mg rFVIIa ampul, 10 m sterile rolled gauze, 500 mL sterile saline Assessment of Subjects Followed by Treatment In some embodiments, the methods of the present disclosure involve diagnosis of PPH and subsequent treatment, for example according to the steps outlined. In other embodiments, the methods of the present disclosure involve assessment of whether a subject will benefit from the treatment. In some embodiments, subjects that will benefit from treatment comprise subjects that have lost 500 mL blood or more from the subject's uterus subsequent to giving birth. Those subjects are at serious health risk, and the present method thus reduces the risk of dying or suffering from severe complications resulting from haemorrhage.

In some embodiments, the present disclosure provides a method for diagnosis of PPH in a female subject and subsequent treatment of PPH, comprising the steps of:

a. determining if the subject has lost 500 mL blood or more from the subject's uterus subsequent to giving birth,
b. wherein if the subject has lost 500 mL blood or more, PPH is diagnosed, and
c. a medical dressing suitable for uterine insertion to form a tamponade soaked or smeared in a composition comprising from 1 mg to 12 mg of an activated Factor VII (FVIIa) polypeptide or a pharmaceutically acceptable variant or prodrug thereof, is inserted into the female subject's uterus such as to form a tamponade, and
d. the medical dressing is maintained in the uterus for at least 15 minutes, thereby treating the postpartum haemorrhage.

In particular embodiments, subjects that will benefit from treatment have lost 500 mL blood or more from the subject's uterus, and do not suffer from a trauma, such as a cervical and/or vaginal trauma. This assessment can be aided by inspection and/or palpation.

In some embodiments, the subject has lost 500 mL blood or more from the subject's uterus subsequent to giving birth despite receiving treatment with one or more uterotonics.

In some embodiments, the method disclosed herein further comprising one or more or all the steps of:

a. inspection and palpation of the subject's vulva, vagina, cervix, and uterus,
b. suturing of tears in vulva, cervix, and vagina, and
c. removal of retained placenta elements from the uterine cavity.

In preferred embodiments, the method further comprises a step of inspection and/or palpation at or in close proximity to the site of haemorrhage, optionally wherein the step of inspection and/or palpation is prior to, simultaneous with or subsequent to step a. Inspection and/or palpation is performed to assess whether the subject will benefit from treatment. Hence, this step is well-suited for methods of the present disclosure disclosed herein aiming at assessing whether a subject will benefit from the treatment. The Inspection and/or palpation step can be used to assess whether the subject is haemorrhage due to a trauma, such as a cervical and/or a vaginal trauma. If the subject is not haemorrhage due to such trauma, the treatment is particularly useful. In some embodiments, the site of haemorrhage is the placenta site.

In some embodiments, a method is provided for diagnosis of PPH in a subject and subsequent treatment of PPH, comprising the steps of:

a. Determining if the subject has lost 500 mL blood or more from the subject's uterus subsequent to giving birth,
b. Wherein the subject has lost 500 mL blood or more, PPH is diagnosed and the composition, the solution, and/or the haemorrhage inhibiting patch as defined herein is administered to the subject.

In some embodiments, a method is provided for identifying a subject that will benefit from treatment, and subsequent treatment of the subject, comprising the steps of:

a. Determining if the subject has lost 500 mL blood or more from the subject's uterus subsequent to giving birth,
b. Wherein the subject has lost 500 mL blood or more, the subject will benefit from treatment the composition, the solution, and/or the haemorrhage inhibiting patch as defined herein is administered to the subject.

In some embodiments, a method is provided for diagnosis of severe PPH in a subject and subsequent treatment of severe PPH, comprising the steps of:

a. Determining if the subject has lost 1000 mL blood or more from the subject's uterus subsequent to giving birth,
b. Wherein the subject has lost 1000 mL blood or more, severe PPH is diagnosed and the composition, the solution, and/or the haemorrhage inhibiting patch as defined herein is administered to the subject.

In some embodiments, a method is provided for diagnosis of highly severe PPH in a subject and subsequent treatment of severe PPH, comprising the steps of:

a. Determining if the subject has lost 1500 mL blood or more from the subject's uterus subsequent to giving birth, b. Wherein the subject has lost 1500 mL blood or more, highly severe PPH is diagnosed and the composition, the solution, and/or the haemorrhage inhibiting patch as defined herein is administered to the subject. Additionally, the bleeding area can be reached from the bloodstream by parenteral infusion of rFVIIa.

In some embodiments, a method is provided for diagnosis of massive PPH in a subject and subsequent treatment of severe PPH, comprising the steps of:

a. Determining if the subject has lost 2500 mL blood or more from the subject's uterus subsequent to giving birth, b. Wherein if the subject has lost 2500 mL blood or more, massive PPH is diagnosed and the composition, the solution, and/or the haemorrhage inhibiting patch as defined herein is administered to the subject. Additionally, the bleeding area can be reached from the bloodstream by parenteral infusion of rFVIIa.

Non-Limiting Aspects of the Disclosure

In one embodiment PPH arises after vaginal delivery due to general atony (patients' weight is 75 kg): The invention determines the removal of placenta in case of PPH followed by early positioning of the topical rFVIIa method as an addition to the standard PPH treatment after vaginal delivery (VD), see FIG. 1 where the yellow line separates the non-invasive treatments from the non-desirable invasive treatments.

1) At the birth of the child, an uterotonic is given with the delivery of the anterior shoulder, no cord clamping or not before 3 minutes, unless the child's condition necessitates.

2) Within a few minutes: The fundus of the uterus contracts, the placenta is "shred off", and haemorrhage stops. The fundus is immediately massaged.

3) If 2) does not happen and haemorrhage continues or placenta is not delivered—this should happen within 10 min: First-line therapies are applied with active management: Infusion of liquids, uterotonics, CCT (fundus should be contracting, placenta is examined for lack of parts (cotyledons/amnion). External massage of the uterus. By then mother will have already lost >500 ml of blood (PPH status, serviettes are weighed to measure blood loss, and continuation of monitoring). Midwife calls an obstetrician and anaesthesiologist. Key assumption is that we have atony of the uterine muscle.

4) The obstetrician makes inspection and palpation in adequate anaesthesia and intravenous antibiotics, tears are sutured, the bladder is catheterized, manual removal of retained tissue. This should happen preferably within 10 min or between 10 and 20 minutes after delivery.

5) If haemorrhage persists, atony: Typically, patients already have lost >500<1000 mL of blood: Exogenous oxytocin is stopped. Tamponade of the uterus with installation of rolled gauze with rFVIIa-saline solution:

Concomitantly do the following: (according to weight, here in the case of the patient weighing 75 kg):

5a) A package of "ATONY Kit (70-80 kg)" is opened: A solution of 8 mg rFVIIa in saline 500 mL is prepared in a sterile plastic bowl: The saline solution is poured into the bowl, and the dried powder is mixed with the small histidine solution and added to the saline (2 min). The rolled gauze is soaked in the solution (1 min).

5b) The cervix is grasped by cervical forceps and a temporary swab is placed in the uterus (for 2-5 minutes) with a long peang while attending the preparation of the rFVIIa solution. The swab is removed from the uterus and a tamponade of the uterus is made with the rolled gauze soaked in the rFVIIa solution (takes 5-10 min to make the tamponade). Leave for 6 hours to give the muscle a rest to recover its strength.

6) If haemorrhage persists: Typically, the patient is very weak and has lost >1000<1500 ml of blood. Tachycardia and hypotension manifest the severity of haemorrhage. Worsening of these parameters, blood pressure <80 mmHg, tachypnoea and altered mental state indicate PPH>1500 mL.

Second line therapies are installed:

1. Addition of intravenous blood products
2. Uterine compression suture
3. Ligation of the uterine or internal iliac arteries
4. Uterine artery embolization
5. Peripartum hysterectomy
6. Transfer to ICU In another embodiment due to atony after vaginal delivery (patients' weight is 75 kg), a tamponade of the uterus is made with a Bakri balloon swept in a surgical swab that has been soaked in a "ATONY Kit (70-80 kg)" or 8 mg/500 mL saline solution and kept for 6 hours. Alternatively, if the Bakri balloon holds a catheter, the uterine cavity can be washed repeatedly with the above solution until haemostasis.

In the rare event, that PP/PAS appears after vaginal delivery (Cave Inversio Uteri when doing CCT), (patient's weight is 75 kg): After Inspection and palpation a tamponade with rolled gauze soaked in a rFVIIa solution from the "ATONY Kit (70-80 kg)" package is made. Exogenous oxytocin is administered if no atony. The rolled gauze is gently removed after 6 hours.

In another embodiment (patients' weight is 75 kg) PP/PAS has been diagnosed and a caesarean section performed: The invention determines the positioning of the topical rFVIIa method as an addition to the standard treatment of PPH during caesarean delivery (CD), see FIGS. 6-10:

1) Birth of the child, an uterotonic is given with the delivery of the anterior shoulder, no cord clamping or not before 3 minutes unless the child's or mother's condition necessitates.

2) Within a few minutes: The fundus of the uterus contracts, the placenta is "shred off", and haemorrhage stops. The fundus is immediately massaged.

3) If 2) does not happen and haemorrhage continues or placenta is not separated after a few minutes: Uterotonics, placenta is removed manually, placenta is examined for lack of parts (cotyledons/amnion). External massage of the uterus. Key assumption: PAS.

4) If haemorrhage persists: Typically, patients then already have lost >500<1000 ml of blood:

4a) A temporary swab is placed at the haemorrhaging placenta site. A package of "PP/PAS 2 mg" is opened: A solution of 2 mg rFVIIa in saline 250 mL is prepared in a sterile plastic bowl: The saline solution is poured into the bowl, and the dried powder is mixed with the small histidine solution and added to the saline (2 min). A swab is soaked in the solution (1 min).

4b) The temporary swab is replaced by the soaked swab at the haemorrhage placenta site. It is held for 2 min and hereafter slowly removed. The procedure can be repeated. If the placenta site continues to bleed do concomitantly the following:

4c) The patient is put in a gynaecological position

4d) A rolled gauze is soaked in "ATONY Kit (70-80 kg)", 8 mg/500 mL solution for 1 minute.

5) The swab is removed from the uterus, the ureterotomy quickly closed and a tamponade of the uterus is made through the vagina. Make sure that haemostasis is obtained before closure of the peritoneum. Leave for 6-24 hours. In case of no atony, give an intravenous drip with oxytocin. If the tamponade exceeds 6 hours, give antibiotics.

6) If haemorrhage persists: Typically, the patient is very weak and has lost >1000<1500 ml of blood. Tachycardia and hypotension manifest the severity of haemorrhage.

Worsening of these parameters, blood pressure <80 mmHg, tachypnoea and altered mental state indicate PPH>1500 mL.

Second line therapies are installed:

1. Addition of intravenous blood products
2. Uterine compression suture
3. Ligation of the uterine or internal iliac arteries
4. Uterine artery embolization
5. Peripartum hysterectomy
6. Transfer to ICU In another embodiment atony occurs when the patient is undergoing an elective or an acute caesarean section: The invention determines the positioning of the topical rFVIIa method in case of PPH as an addition to the normal standard PPH treatment during caesarean delivery (CD), see FIG. 1:

1) Birth of the child, an uterotonic is given with the delivery of the anterior shoulder, no cord clamping or not before 3 minutes unless the child's condition necessitates.

2) Within a few minutes: The fundus of the uterus contracts, the placenta is "shred off", and haemorrhage stops. The fundus is immediately massaged.

3) If 2) does not happen and haemorrhage continues or placenta is not separated after a few minutes: Uterotonics, placenta is removed manually, placenta is examined for lack of parts (cotyledons/amnion). External massage of the uterus.

4) If haemorrhage persists: Typically, patients then already have lost >500<1000 ml of blood: Uterus not adequately contracted. Atony. Exogenous oxytocin is stopped. Do concomitantly the following:

4a) A temporary swab is placed at the haemorrhage placenta site.

4b) A package of "ATONY 8 mg rFVIIa" is opened: A solution of 8 mg rFVIIa in saline 500 mL is prepared in a sterile plastic bowl: The saline solution is poured into the bowl, and the dried powder is mixed with the small histidine solution and added to the saline (2 min). A rolled gauze is soaked in the solution (1 min).

5) The patient is put in a gynaecological position. The temporary swab is removed from the haemorrhage placenta site, and the uterotomy quickly closed. At the same time a doctor makes a tamponade of the uterus through the vagina with a rolled gauze soaked in the rFVIIa solution. Make sure that haemostasis is obtained before closure of the peritoneum. Leave for 4-6 hours to give the muscle a rest to recover its strength.

6) If haemorrhage persists: Typically, the patient is very weak and has lost >1000<1500 ml of blood. Tachycardia and hypotension manifest the severity of haemorrhage.

Worsening of these parameters, blood pressure <80 mmHg, tachypnoea and altered mental state indicate PPH>1500 mL.

Second line therapies are installed:

7. Addition of intravenous blood products
8. Uterine compression suture
9. Ligation of the uterine or internal iliac arteries
10. Uterine artery embolization
11. Peripartum hysterectomy
12. Transfer to ICU Topical rFVIIa solution and rolled gauze can be used in PPH caused by atony, PP/PAS and haematological disorders. PP/PAS patients normally undergo elective CS and sometimes haemostasis can be obtained by rFVIIa-soaked in swabs. In some embodiments, exogenous oxytocin is not used: in cases of atony.

When "standard procedures" and "current standard first-line therapies" involving infusion of liquids, uterotonics, uterine massage, suture of tears, catheterization of the bladder, removal of retained placenta elements have had insufficient effect to contain blood loss. Before infusions of full blood or blood products. Before entering "full standard second-line therapies". Before entering ICU, the present disclosure optimally provides for amelioration of the haemorrhage by direct application of rFVIIa at the placenta site.

Advantages of the Present Disclosure

1) The activated FVII (FVIIa) molecule is big (MW 50 kDalton) and does not penetrate intact endothelium.

Rats, pigs and humans have been tested with local application of rFVIIa, NovoSeven, 500-1000 μg and up to 38 times higher concentrations than the Stellaris method without occurrence of any thrombotic events, see WO1993006855.

2) Pregnancy is a hypercoagulative state functioning as a physiologically adaptive mechanism to prevent PPH. In normal pregnancy there is a marked increase in the procoagulant activity in maternal blood: The elevation of the factors Vila (4.3 ng/mL to 12.0 ng/mL or even higher at term, factor VIII, X, fibrinogen and von Willebrand factor are at their maxima at term.

3) Systemic administration of FVIIa leads to the intravascular distribution of FVIIa exposing most parts of the body, while local administration leads to a local deposition of high amounts of FVIIa in the extravascular tissue i.e., at the intraluminal placenta site from where the haemorrhage origins. These two different administration paths reach the haemorrhage placenta site through two fundamentally different compartments.

Off-label use of intravenous rFVIIa is limited by an US Food and Drug Administration (FDA) box warning: "Serious thrombotic adverse effects associated with the use of NovoSeven RT outside labelled indications. The indications are: Treatment of haemorrhage episodes and perioperative management in adults and children with haemophilia A or B with inhibitors, congenital Factor VII (FVII) deficiency, and Glanzmann's thrombasthenia. In 2023, the European Medicine Agency allowed treatment of intravenous rFVIIa, NovoSeven, against PPH>1500 mL, EMA, Annex 1, Summary of product characteristics. NovoSeven, 2022. For the same reasons as in 2) the Danish association of Gynecology and Obstetrics as well as the bleeding/coagulation team of Rigshospitalet, Copenhagen, Denmark has published a statement article NOT recommending the use of intravenous rFVIIa against PPH unless in major and catastrophic situations. See also Laird et al: International Journal of Obstetric Anaesthesia, Vol 17, no. 2,194-194, 2008, EMA: Annex I, Summary of product Characteristics. NovoSeven INN-eptalog alfa, 23 Feb. 1996, 1-48, internet.

In TF-induced coagulation of blood drawn from patients with haemophilia, the addition of rFVIIa increases both the rate and the level of thrombin generation. Moreover, when rFVIIa is added to TF-induced coagulation of blood from healthy persons the reaction is even faster and with a greater production of thrombin. This explains why 97% of NovoSeven (NOVO Nordic, Bagsvaerd, Denmark) treatments have been sold off-label throughout a period of 10 years in the beginning of this century.

A multi-centre study utilising intravenous rFVIIa in patients with PPH>1500 mL, revealed a reduction in second-line surgical procedures by ⅓. Unfortunately, 5% had thrombotic events in the group of patients receiving treatment. Local use of rFVIIa requires no administration of other blood products: haemorrhage occurs to the luminal site of the uterus and no pre-treatment of depleted procoagulants are needed as seen with intravenous rFVIIa.

4) Use of intravenous blood products increases the risks of transfer of vira, HIV, parvovirus, and hepatitis vira to the patient's blood, see WO1993006855. rFVIIa is a recombinant glycosylated protein from transgenic hamsters/rabbits/insects that do not transfer vira. Allergy to the above-mentioned animals could cause a concern.

5) Thrombin-containing topicals (thrombin MW≈37 kDalton (84), have been placed at the placenta site against severe PPH. Thrombin, a coagulant, is absolutely contraindicated for systemic use because of the instant formation of multiple intravascular thrombes. However, when fixed to a proper carrier, no thrombotic complications have been described after topical use of thrombin. Thrombin is commonly used with a bovine gelatine as a carrier. Bovine-thrombin containing haemostatics for local use can transfer Creutzfeldt-Jacobs Disease and Kuru. FloSeal, is one such application at the placenta site. Reports of granuloma formation in the uterus after FloSeal (bovine gelatine as carrier) and TacoSil (equine tendon as carrier and fibrinogen) as well as risk of placenta accreta in later pregnancy makes this treatment less attractive.

6) Chitosan, a shellfish protein and a strong allergen has shown effect in some reports, and turned out to be as effective as Bakri.

7) rFVIIa excels as a topical agent: rFVIIa is the only activated coagulant that can circulate in the systemic circulation without initiating the cascade—and FVIIa could therefore theoretically be "overspilled"—without causing systemic tremendous devastation. Intravenous rFVIIa used in catastrophic situations causes few and not multiple thrombotic events.

8) Rolled gauze is a solid carrier which adds a mechanical haemorrhage inhibiting effect, it is pH neutral and does not denature rFVIIa and it leaves no traces when removed. Earlier, tamponade of the uterus against PPH due to atony was obtained utilising a rolled gauze instilled for up to 24 h. Because of discussions of risks of infection, the Bakri balloon method is now widely used despite risks of necrosis if wrongly adjusted. Infections are a risk after both rolled gauze and Bakri—especially if installed for up to 24 hours despite intravenous antibiotics.

Disadvantages of Bakri include balloon damage, high cost, and limited effectiveness in a large uterine cavity and risks of necrosis if wrongly installed.

New investigations show that a rolled gauze or a Bakri balloon equally exert mechanical hindering of placenta site hemorrhages, they both are successful in up to 90% of installations, the hemorrhage amount is a little smaller after Bakri than after gauze, but there are 6% of patients demonstrate complications after Bakri balloon.

Uterine tamponade with a rolled gauze is accessible, cheap, and easily applicable. The Bakri balloon is more expensive, less easy to install, it needs a more skilled person and bears a risk of both being overfilled and being too much pulled tot with the risks of necrosis most often at the cervical level in the hands of non-professionals.

In Summary: Advantages of Utilising Topical rFVIIa Over Other Means:

1. Avoids risks of intravenous blood products:
   Contamination with HIV, parvovirus, hepatitis, Creutzfeldt-Jacobs Disease, Kuru
2. Avoids intravenous Application of rFVIIa
   a. Off-label
   b. Box warning of the FDA
   c. Significant risks of undesired thrombosis
   d. Local application does NOT have systemic side-effects.
   it does NOT penetrate intact endothelium
3. Avoids risks of locally applied thrombin/carrier combinations
   a. Risk of granuloma formation in uterus
   b. Risk of placenta accreta
4. Avoids risk of use of intravenous tranexamic acid TXA
   a. Sparse haemostatic effects
   b. Systemic adverse effects—dangerous to administer 3 hours after delivery.
5. Avoids necrosis of the cervix: Rolled gauze soaked in a rFVIIa solution is easily applicable as a tamponade compared to the Bakri balloon with no risks of necrosis.
6. Avoids blood transfusions
7. Avoids further surgical interventions like
   a. Uterine compression suture
   b. Ligation of the uterine or internal iliac arteries
   c. Uterine artery embolization
8. Significantly reduces the further complications leading to
   a. Peripartum hysterectomy
   b. Transfer to intensive care unit
   c. psychological damage
   d. Death The topical rFVIIa/rolled gauze method is non-invasive, cheap, effectful with no adverse effects.

EXAMPLES

Materials and Methods

Recombinant activated Factor VII, sterile gauze with neutral pH, sterile neutral pH swabs, sterile saline, sterile forceps, sterile long gloves. The present examples represent a non-limiting set of cases where the invention is particularly useful.

Example 1

A patient (75 kg) has undergone vaginal delivery after hours of slow progression. An oxytocin-drip was set up for enhancement of the uterine contractions. After an exhausting 2. period of labour a 4-kilo child was delivered. Uterotonics were given and CCT was performed, the placenta was easily delivered and seemed intact. The uterus did not contract properly despite mechanical manipulation. Shortly thereafter PPH occurred. The midwife added extra uterotonic to the drip, emptied the urine bladder and called the obstetrician and an anaesthesiologist. The patient underwent inspection and palpation in adequate anaesthesia and antibiotics, and there were no signs of trauma, and no suspicion of retained tissue. Haemorrhage continued from an atonic uterus. The uterotonic drip was subsequently stopped. The cervix was taken hold of by two soft forceps, a swap was grabbed with a long peang and installed in the uterine cavity while a 500 mL sterile saline solution with the contents of "ATONY Kit (70-80 kg)", 8 mg rFVIIa was stirred into it, prepared swiftly and a 10 m pH-neutral gauze was soaked herein. The swap was removed, and the uterus was packed with the rFVIIa-soaked gauze. Haemorrhage ceased. The gauze was gently removed after 6 hours and the uterus appeared well contracted.

Example 2

The present example refers to a rare situation, since most cases of placenta previa/placenta accreta spectrum are displayed at ultrasonic scanning performed during pregnancy.

A patient (75 kg), primipara, 3. gravida, with 2 times earlier evacuation uteri because of missed abortions, delivered without problems a normal weight child. The patient underwent active management with CCT showing complications, the placenta seemed adherent. The obstetrician and an anaesthesiologist were immediately called. Finally, the placenta was pulled out, but one cotyledon seemed lacking and hemorrhage continued. Palpation in adequate anesthesia and antibiotics revealed a piece of cotyledon which was not fully removable. The cervix was taken hold of by two soft forceps, a swap was grabbed with a long peang and installed in the uterine cavity while a 500 mL sterile saline solution with "ATONY Kit (70-80 kg)", 8 mg rFVIIa was stirred into it and prepared swiftly followed by a 10 m pH-neutral gauze which was soaked herein. The swap was removed, and the uterus packed with the rFVIIa-soaked gauze. Antibiotics. Exogenous oxytocin was given. Hemorrhage ceased. The gauze was gently removed after 24 hours to reveal an uterus which was well contracted.

Example 3

A patient (75 kg) underwent a caesarean section because of ultrasonic findings of PP plus suspicion of PAS. The child was delivered, and the lower part of the placenta was adherent to the dorsal wall of the uterus. The placenta was removed but a small part was adherent, and it bled heavily from the area. A swab was placed while a 250 mL sterile saline solution with "PP/PAS Kit 2 mg" was stirred into it followed by soaking of a swap into the saline solution. The swap was replaced by the rFVIIa-soaked swab which was held firmly at the haemorrhage placenta site for 2 min. The swab was subsequently gently removed, the placenta bed was dry, and the uterus contracted. The uterus now appeared closed, and the patient was observed closely for 24 hours for PPH.

Example 4

A woman (75 kg) had been in labour for hours, a uterotonic drop had been installed, the first phase protracted, the second phase ditto. The mother was exhausted, and the child also began to show signs of stress with decelerations that rose too slowly after each contraction. An emergency caesarean section was performed. The child was fine, but the woman's uterus did not contract properly after removal of the intact placenta despite uterotonics and massage. General atony of the uterus. Uterotonics was stopped, a swab was firmly placed at the haemorrhage placenta site. The patient was brought into a gynaecological position while at the same time a solution was prepared of "ATONY Kit (70-80 kg)", 8 mg rFVIIa in 500 mL sterile saline which was soaked on a 10 m pH-neutral gauze which was placed at the haemorrhage site. The uterotomy was quickly sutured and immediately hereafter an assistant doctor made through vagina a tamponade of the uterus. Antibiotics were administered. The hemorrhage stopped, the peritoneum was closed, and the operation terminated. Antibiotics. 24 hours later the gauze was gently removed, the uterus appeared contracted with an acceptable level of hemorrhage.

The invention claimed is:

1. A method for the treatment or amelioration of a placenta site postpartum haemorrhage (PPH) from a uterus having a non-open corpus in a female subject being administered a uterotonic, comprising the consecutive steps of:

a. determining continued haemorrhage from an atonic uterus in said subject following administration of one or more uterotonics to said subject, b. in response to step a providing a medical dressing suitable for uterine insertion to form a tamponade, wherein the medical dressing comprises 1 mg to 12 mg of activated Factor VII (FVIIa) polypeptide or a pharmaceutically acceptable variant or prodrug thereof, c. inserting the medical dressing into the uterus of the female subject in the form of a tamponade in contact with the placenta site, and wherein no uterotonics are administered to the subject for at least 4 hours from the inserting, and d. maintaining the medical dressing in the uterus in contact with the placenta site for 4 hours to 24 hours, thereby treating or ameliorating the placenta site postpartum haemorrhage;

wherein the postpartum haemorrhage results from uterotonic resistant global atony.

2. The method according to claim 1, wherein the medical dressing is hypoallergenic, non-adhesive and non-irritating to a wound.

3. The method according to claim 1, wherein the medical dressing comprises a gauze.

4. The method according to claim 1, wherein the medical dressing is rolled, packed, twisted or folded prior to or during step b to provide the tamponade.

5. The method according to claim 1, wherein the medical dressing is contacted with the placenta site postpartum haemorrhage for 6 hours to 24 hours and wherein one or more antibiotics are administered to the female subject.

6. The method according to claim 1, wherein the FVIIa polypeptide or a pharmaceutically acceptable variant or prodrug thereof is selected from the group consisting of: recombinant FVIIa (rFVIIa) or a glycoform thereof, wild type FVIIa, and a factor VII polypeptide in uncleaved form (zymogen).

7. The method according to claim 1, wherein the subject has lost 500 mL or more blood from the subject's uterus subsequent to giving birth.

8. The method of claim 1, further comprising inspection and palpation of one or more of the subject's vulva, vagina, cervix, and uterus to exclude trauma prior to step a).

9. A method for diagnosis of a placenta site postpartum haemorrhage (PPH) from an open-corpus uterus in a female subject and subsequent treatment of PPH, comprising the steps of:

a. Determining if the subject has lost 500 mL blood or more from the subject's atonic uterus subsequent to giving birth following administration of one or more uterotonics, b. Wherein if the subject has lost 500 mL blood or more, PPH is diagnosed, c. in response to step a providing a medical dressing suitable for uterine insertion to form a tamponade, wherein the medical dressing comprises 1 mg to 12 mg of activated Factor VII (FVIIa) polypeptide or a pharmaceutically acceptable variant or prodrug thereof, d. inserting the medical dressing into the uterus of the female subject in the form of a tamponade in contact with the placenta site, and wherein no uterotonics are administered to the subject for at least 4 hours from the inserting, and e. maintaining the medical dressing in the uterus in contact with the placenta site for at least 15 minutes, thereby treating or ameliorating the placenta site postpartum haemorrhage;

wherein the postpartum haemorrhage results from uterotonic resistant global atony, thereby treating or ameliorating the postpartum haemorrhage.

10. The method according to claim 9, wherein the subject has lost 500 mL blood or more from the subject's uterus subsequent to giving birth despite receiving treatment with one or more uterotonics.

11. The method according to claim 9, further comprising one or more or all the steps of:

i. inspection and palpation of the subject's vulva, vagina, cervix, and uterus, ii. suturing of tears in vulva, cervix, and vagina, and iii removal of retained placenta elements from the uterine cavity.

12. The method according to claim 9, wherein the activated Factor VII (FVIIa) polypeptide or a pharmaceutically acceptable variant or prodrug thereof is selected from the group consisting of: recombinant FVIIa (rFVIIa), a glycoform thereof, wild type FVIIa, and a factor VII polypeptide in uncleaved form (zymogen).

* * * * *